(12) United States Patent
Shkolnikov et al.

(10) Patent No.: US 12,204,085 B2
(45) Date of Patent: Jan. 21, 2025

(54) NONROTATING NONUNIFORM ELECTRIC FIELD OBJECT ROTATION

(71) Applicant: HEWLETT-PACKARD DEVELOPMENT COMPANY, L.P., Spring, TX (US)

(72) Inventors: Viktor Shkolnikov, Palo Alto, CA (US); Daixi Xin, Palo Alto, CA (US); Yang Lei, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 610 days.

(21) Appl. No.: 16/606,239

(22) PCT Filed: Apr. 27, 2018

(86) PCT No.: PCT/US2018/030037
§ 371 (c)(1),
(2) Date: Oct. 18, 2019

(87) PCT Pub. No.: WO2019/209347
PCT Pub. Date: Oct. 31, 2019

(65) Prior Publication Data
US 2021/0033842 A1 Feb. 4, 2021

(51) Int. Cl.
*G02B 21/36* (2006.01)
*G01N 33/483* (2006.01)
(Continued)

(52) U.S. Cl.
CPC ....... *G02B 21/367* (2013.01); *G01N 33/4833* (2013.01); *G06T 17/00* (2013.01); *H04N 23/66* (2023.01); *G06T 2210/41* (2013.01)

(58) Field of Classification Search
CPC .. G02B 21/367; G01N 33/4833; G06T 17/00; G06T 2210/41; G06T 17/05; G06T 17/10;
(Continued)

(56) References Cited

U.S. PATENT DOCUMENTS 5,768,156 A * 6/1998 Tautges ................... G06T 17/20
703/2
5,805,289 A * 9/1998 Corby, Jr. ............ G01B 11/002
356/613
(Continued)

FOREIGN PATENT DOCUMENTS

| EP | 1413911 B1 | 4/2004 |
|---|---|---|
| WO | WO1993016383 A1 | 8/1993 |
| WO | WO2017151978 A1 | 9/2017 |

OTHER PUBLICATIONS

Mendonca, Paulo et. al., Camera Pose Estimation and Reconstruction from Image Projiles under Cirular Motion., University of Cambridge, 13 pages.
(Continued)

*Primary Examiner* — Charles L Beard
(74) *Attorney, Agent, or Firm* — Foley & Lardner LLP

(57) ABSTRACT

A three-dimensional object modeling method may include applying a nonrotating nonuniform electric field to apply a dielectrophoretic torque to a three-dimensional object to rotate the three-dimensional object, capturing images of the object at different angles during rotation of the object and forming a three-dimensional model of the object based on the captured images.

1 Claim, 4 Drawing Sheets

(51) Int. Cl.
*G06T 17/00* (2006.01)
*H04N 23/66* (2023.01)

(58) Field of Classification Search
CPC ......... G06T 17/20; G06T 17/30; G06T 19/00; H04N 5/23203
See application file for complete search history.

(56) References Cited

U.S. PATENT DOCUMENTS

| | | | | |
|---|---|---|---|---|
| 6,157,747 | A * | 12/2000 | Szeliski | G06V 10/24 382/284 |
| 6,411,099 | B1 * | 6/2002 | Afilani | G08B 13/2491 324/452 |
| 6,448,794 | B1 * | 9/2002 | Cheng | G01N 33/48707 324/692 |
| 6,525,875 | B1 | 2/2003 | Lauer | |
| 6,537,433 | B1 * | 3/2003 | Bryning | G01N 27/44791 204/600 |
| 6,610,256 | B2 * | 8/2003 | Schwartz | G01N 27/44721 422/186 |
| 6,954,297 | B2 * | 10/2005 | Reboa | G02B 26/004 359/904 |
| 7,023,603 | B2 * | 4/2006 | Reboa | G02B 26/0841 359/254 |
| 7,160,425 | B2 * | 1/2007 | Childers | B01L 3/50273 435/307.1 |
| 7,390,388 | B2 * | 6/2008 | Childers | B03C 5/005 204/450 |
| 7,486,000 | B1 * | 2/2009 | Hacsi | H02N 10/00 60/516 |
| 7,888,892 | B2 * | 2/2011 | McReynolds | H02K 7/1853 318/686 |
| 8,658,418 | B2 * | 2/2014 | Daridon | B01L 3/502738 435/288.5 |
| 9,026,407 | B1 * | 5/2015 | Kennefick | G06T 17/00 703/1 |
| 9,433,363 | B1 * | 9/2016 | Erasala | A61B 5/245 |
| 9,858,716 | B2 | 1/2018 | Kalvin | |
| 9,940,420 | B2 * | 4/2018 | Kennefick | B81B 3/0097 |
| 10,304,188 | B1 * | 5/2019 | Kumar | G06V 20/695 |
| 10,475,250 | B1 * | 11/2019 | Huang | G06Q 30/0643 |
| 10,481,120 | B1 * | 11/2019 | Sarles | C08J 5/00 |
| 10,678,493 | B2 * | 6/2020 | Chang | G06F 3/1454 |
| 10,976,566 | B2 * | 4/2021 | Xiang | G02B 21/06 |
| 11,080,447 | B2 * | 8/2021 | Sanders | G06F 30/27 |
| 2002/0135558 | A1 * | 9/2002 | Richley | G02B 26/026 345/107 |
| 2002/0190732 | A1 * | 12/2002 | Cheng | G01N 33/48707 324/693 |
| 2003/0007894 | A1 * | 1/2003 | Wang | H05H 3/04 435/173.9 |
| 2003/0176994 | A1 * | 9/2003 | Spitz | G06T 17/10 703/27 |
| 2003/0199758 | A1 | 10/2003 | Nelson | |
| 2004/0196226 | A1 * | 10/2004 | Kosc | G02F 1/172 345/87 |
| 2005/0211556 | A1 * | 9/2005 | Childers | B03C 5/028 204/627 |
| 2005/0226483 | A1 * | 10/2005 | Geiger | G06T 19/00 382/128 |
| 2006/0111887 | A1 * | 5/2006 | Takeuchi | G06T 17/10 703/22 |
| 2006/0126921 | A1 * | 6/2006 | Shorte | G02B 21/22 382/154 |
| 2006/0183096 | A1 * | 8/2006 | Riener | G09B 23/30 434/267 |
| 2007/0092958 | A1 * | 4/2007 | Syed | B82Y 5/00 435/286.1 |
| 2009/0125242 | A1 | 5/2009 | Choi et al. | |
| 2009/0268214 | A1 | 10/2009 | Lucic et al. | |
| 2009/0310869 | A1 * | 12/2009 | Thiel | G01B 11/2513 382/201 |
| 2009/0314644 | A1 * | 12/2009 | Golan | C12M 47/04 204/600 |
| 2009/0315885 | A1 * | 12/2009 | Baszucki | G06T 19/20 345/420 |
| 2010/0006441 | A1 * | 1/2010 | Renaud | B01L 3/502746 204/643 |
| 2010/0097687 | A1 * | 4/2010 | Lipovetskaya | G02B 26/026 359/296 |
| 2010/0224493 | A1 * | 9/2010 | Davalos | B03C 5/005 204/547 |
| 2010/0259259 | A1 * | 10/2010 | Zahn | G01R 33/5601 324/309 |
| 2011/0170105 | A1 * | 7/2011 | Cui | G02B 21/33 356/450 |
| 2011/0295579 | A1 * | 12/2011 | Tang | A61B 8/13 703/9 |
| 2012/0085649 | A1 * | 4/2012 | Sano | B03C 5/005 204/547 |
| 2012/0258408 | A1 * | 10/2012 | Mayer | C25D 17/002 204/229.5 |
| 2013/0187930 | A1 * | 7/2013 | Millman | G06T 19/00 345/473 |
| 2013/0217210 | A1 * | 8/2013 | Brcka | C12M 21/08 118/640 |
| 2013/0271461 | A1 * | 10/2013 | Baker | G06T 15/50 345/420 |
| 2013/0280752 | A1 * | 10/2013 | Ozcan | G01B 9/02041 356/482 |
| 2013/0311450 | A1 * | 11/2013 | Ramani | G06V 30/1988 707/722 |
| 2014/0071452 | A1 * | 3/2014 | Fleischer | G01N 15/147 356/436 |
| 2014/0125663 | A1 * | 5/2014 | Zhang | G06T 7/13 345/420 |
| 2014/0200429 | A1 * | 7/2014 | Spector | A61B 5/316 600/374 |
| 2014/0346044 | A1 * | 11/2014 | Chi | B03C 7/023 204/547 |
| 2015/0017879 | A1 * | 1/2015 | Chang | G06T 7/0004 451/5 |
| 2015/0169190 | A1 * | 6/2015 | Girardeau | G06T 11/00 715/771 |
| 2015/0184225 | A1 * | 7/2015 | Wong | C12Q 1/686 435/6.12 |
| 2015/0320331 | A1 * | 11/2015 | van Dam | A61B 5/318 600/509 |
| 2015/0358612 | A1 * | 12/2015 | Sandrew | H04N 13/261 348/47 |
| 2016/0044301 | A1 | 2/2016 | Jovanovich et al. | |
| 2016/0184821 | A1 * | 6/2016 | Hobbs | B01L 3/502761 422/504 |
| 2016/0348050 | A1 * | 12/2016 | Sivan | C12M 29/00 |
| 2017/0017841 | A1 * | 1/2017 | Chen | G06T 7/12 |
| 2017/0028408 | A1 * | 2/2017 | Menachery | G01N 27/44721 |
| 2017/0067815 | A1 * | 3/2017 | Lawandy | G01N 15/0205 |
| 2017/0071492 | A1 * | 3/2017 | van Dam | A61B 5/282 |
| 2017/0108493 | A1 * | 4/2017 | Wu | G01N 27/3275 |
| 2017/0206686 | A1 * | 7/2017 | Mazeh | G06T 11/001 |
| 2017/0218424 | A1 * | 8/2017 | Swami | C12Q 1/04 |
| 2017/0293195 | A1 * | 10/2017 | Yamazaki | G02F 1/13306 |
| 2017/0303865 | A1 * | 10/2017 | Kojima | A61B 5/742 |
| 2017/0310253 | A1 * | 10/2017 | Cai | H02K 11/215 |
| 2017/0317622 | A1 * | 11/2017 | Cai | H02K 11/215 |
| 2017/0363606 | A1 * | 12/2017 | Kikitsu | H10N 50/10 |
| 2017/0363857 | A1 * | 12/2017 | Kaku | A61B 1/00089 |
| 2017/0370818 | A1 * | 12/2017 | Gazzola | B01L 3/502761 |
| 2018/0140359 | A1 * | 5/2018 | Koyrakh | A61B 34/20 |
| 2018/0149644 | A1 * | 5/2018 | Yang | G01N 33/54373 |
| 2018/0218519 | A1 * | 8/2018 | Almutiry | G06F 18/22 |
| 2018/0238831 | A1 * | 8/2018 | Wollnik | G01N 27/624 |
| 2018/0268517 | A1 * | 9/2018 | Coban | G06T 15/205 |
| 2019/0046986 | A1 * | 2/2019 | Yuan | G01N 27/44791 |
| 2019/0049399 | A1 * | 2/2019 | Ogura | G01N 33/48 |
| 2019/0059999 | A1 * | 2/2019 | Nishioka | G16H 30/20 |
| 2019/0168237 | A1 * | 6/2019 | Hayes | B01L 3/502753 |
| 2019/0175276 | A1 * | 6/2019 | Krimsky | A61B 5/7275 |
| 2019/0233965 | A1 * | 8/2019 | Zhao | C25D 13/02 |

(56) References Cited

U.S. PATENT DOCUMENTS

| | | | |
|---|---|---|---|
| 2019/0234902 A1* | 8/2019 | Lima, Jr. | G01N 33/5438 |
| 2019/0239332 A1* | 8/2019 | Hidding | H01S 3/0903 |
| 2019/0287289 A1* | 9/2019 | Araki | G06T 15/08 |
| 2019/0311500 A1* | 10/2019 | Mammou | G06T 9/001 |
| 2019/0314820 A1* | 10/2019 | Geng | G01N 27/44769 |
| 2019/0346361 A1* | 11/2019 | Meldrum | G01N 15/1436 |
| 2019/0376947 A1* | 12/2019 | Mitsunaka | G01N 33/4833 |
| 2020/0048626 A1* | 2/2020 | Mena | C12N 15/1006 |
| 2020/0050959 A1* | 2/2020 | Ashrafi | H04L 9/0852 |
| 2020/0058140 A1* | 2/2020 | Meldrum | G06T 17/00 |
| 2020/0061383 A1* | 2/2020 | Yomtov | A61N 1/36843 |
| 2020/0108393 A1* | 4/2020 | Lee | B01L 3/502761 |
| 2020/0151874 A1* | 5/2020 | Peterson | G06T 19/00 |
| 2020/0151938 A1* | 5/2020 | Shechtman | G06N 3/045 |
| 2020/0159002 A1* | 5/2020 | Matsunaga | C12M 23/16 |
| 2020/0209644 A1* | 7/2020 | Xiang | G02B 21/02 |
| 2020/0265613 A1* | 8/2020 | Yoon | G06F 18/22 |
| 2020/0271949 A1* | 8/2020 | Colin | H04N 13/296 |
| 2020/0372705 A1* | 11/2020 | Hershkovich | A61N 1/403 |
| 2020/0386666 A1* | 12/2020 | Kung | G01N 27/00 |
| 2021/0003848 A1* | 1/2021 | Choi | G02B 27/0172 |
| 2021/0049809 A1* | 2/2021 | Wahrenberg | G06T 3/00 |
| 2021/0080759 A1* | 3/2021 | Zhao | G02F 1/0136 |
| 2021/0160995 A1* | 5/2021 | Lee | H05H 1/2406 |
| 2021/0208469 A1* | 7/2021 | Didomenico | G02F 1/169 |
| 2021/0231937 A1* | 7/2021 | Xiang | G02B 21/0072 |
| 2021/0262937 A1* | 8/2021 | Shkolnikov | B01L 3/50853 |
| 2021/0264687 A1* | 8/2021 | Lei | G06T 7/564 |
| 2021/0293525 A1* | 9/2021 | Carothers | G01N 21/45 |
| 2021/0293693 A1* | 9/2021 | Bharadwaj | C12Q 1/00 |
| 2021/0293716 A1* | 9/2021 | Carothers | B01L 3/502715 |
| 2021/0295606 A1* | 9/2021 | Kim | G06T 17/20 |
| 2021/0308620 A1* | 10/2021 | Cundliffe | B01D 63/06 |
| 2021/0330864 A1* | 10/2021 | Gumennik | A61L 27/50 |
| 2021/0331169 A1* | 10/2021 | Kashanin | G01N 15/1023 |
| 2021/0366181 A1* | 11/2021 | Lei | G06T 7/579 |
| 2021/0403849 A1* | 12/2021 | Shkolnikov | C12M 23/16 |
| 2022/0005258 A1* | 1/2022 | Mory | A61B 8/5261 |
| 2022/0074843 A1* | 3/2022 | Shkolnikov | B03C 5/005 |
| 2022/0074844 A1* | 3/2022 | D'Apuzzo | G01J 3/0208 |
| 2022/0101048 A1* | 3/2022 | Tan | G16H 50/20 |

OTHER PUBLICATIONS

Benoit et al. "Self-Rotation and Electrokinetic properties of Cells in a Non-Rotational AC Electric Field." MicroTAS 2013 The "17th International Conference on Miniaturized Systems for Chemistry & Life Sciences", 2013, pp. 1361-1363.

Zimmermann et al. "Rotation of Cells in an Alternating Electric Field: the Occurrence of a Resonance Frequency", 1981, pp. 173-177.

* cited by examiner

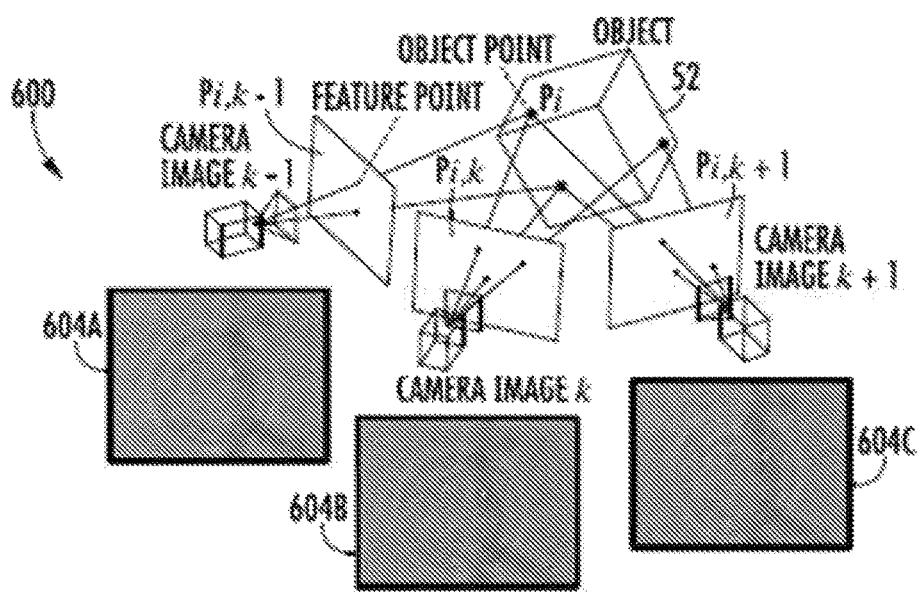
FIG. 7
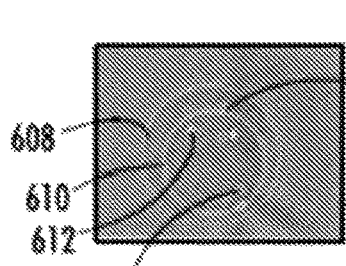
FIG. 8
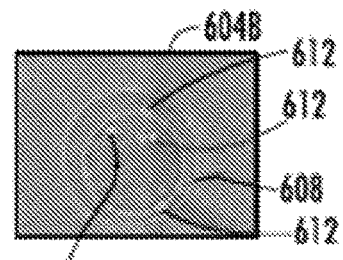
FIG. 9
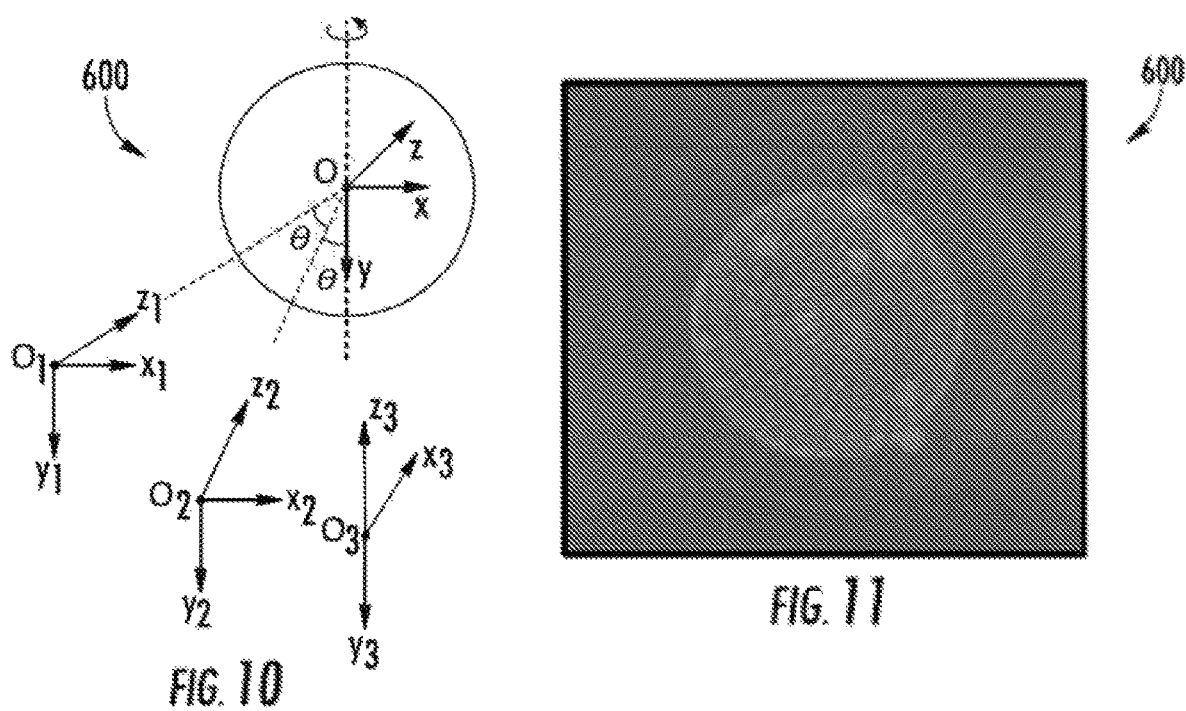
FIG. 10
FIG. 11

NONROTATING NONUNIFORM ELECTRIC FIELD OBJECT ROTATION

BACKGROUND

Objects are sometimes analyzed or simulated through the use of three-dimensional image reconstructions or three-dimensional modeling of the objects such three-dimensional models are sometimes made using multiple images captured while the object is rotating.

BRIEF DESCRIPTION OF THE DRAWINGS

FIG. 7 is a diagram schematically illustrating the capture of two-dimensional image frames of a rotating object at different angles.

FIG. 8 is a diagram depicting an example image frame including the identification of features of an object at a first angular position.

FIG. 9 is a diagram depicting an example image frame including the identifications of the features of the object at a second different angular position.

FIG. 10 is a diagram illustrating triangulation of the different identified features for the merging and alignment of features from the frames.

FIG. 11 is a diagram illustrating an example three-dimensional volumetric parametric model produced from the example image frames of FIGS. 7 and 8.

Figure 1:
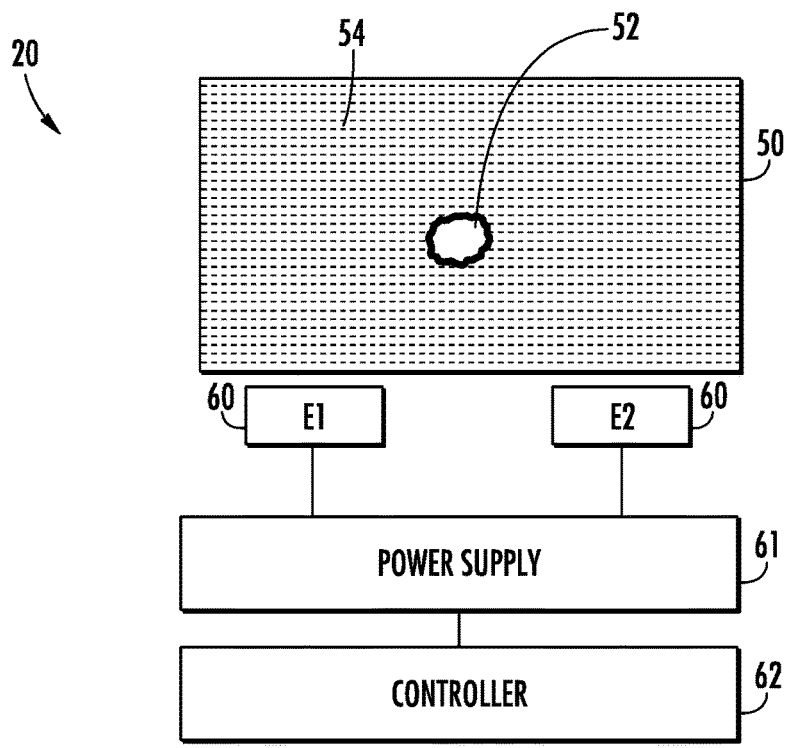
FIG. 1 is a schematic diagram illustrating portions of an example object rotation system.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed herein are example systems and methods for rotating very small objects to facilitate three-dimensional imaging or modeling of such objects. Disclosed herein are example systems and methods that rotate objects for three-dimensional imaging or modeling with less complexity and cost. Disclosed herein are example systems and methods that apply a non-rotating nonuniform electric field so as to apply a dielectrophoretic torque to a three-dimensional object so as to rotate the three-dimensional object.

The example systems and methods facilitate rotation of the very small objects by suspending the very small objects in a fluid, such as a liquid. As a result, the system the methods are well suited for the imaging of objects where direct physical contact and direct manipulation the objects is difficult. The example systems and methods for rotating objects may employ as few as two spaced electrodes to form the nonrotating nonuniform electric field that creates a dielectrophoretic torque and that rotate the three-dimensional object.

The example systems and methods facilitate rotation of the very small objects by suspending the very small objects in a fluid, such as a liquid. As a result, the system the methods are well suited for the imaging of objects where direct physical contact and direct manipulation the objects is difficult. The example systems and methods for rotating objects may employ as few as to spaced electrodes to form the nonrotating nonuniform electric field that creates a dielectrophoretic torque and that rotate the three-dimensional object.

The example systems and methods for rotating objects facilitate rotation of the object about a rotational axis that is parallel to planes of the electrodes. In some implementations, this facilitates rotation of the objects about a rotational axis that is also parallel to a plane of a microfluidic chip, slide or a platform/stage containing the fluid that suspends the object during their rotation. The rotation of the object by the nonrotating nonuniform electric field facilitates rotation the object about the rotational axis that is perpendicular to an optical axis of the camera or imager capturing images of the object during his rotation. Because the rotation axis perpendicular to the optical axis, the overall imaging system may be more compact and less complex.

In some implementations, the three-dimensional object being rotated, imaged and modeled may comprise biological elements, such as cells. In some implementations, three-dimensional object being rotated may comprise a cellular object. For purposes of this disclosure, a cellular object comprises a 3D culture or an organoid. 3D cultures are cells grown in droplets or hydrogels that mimic a physiologically relevant environment. Organoids are miniature organs grown in a lab derived from stem cells and clusters of tissue, wherein the specific cells mimic the function of the organ they model. 3-D cultures and organaids may be used to study basic biological processes within specific organs or to understand the effects of particular drugs. 3-D cultures and organoids may provide crucial insight into mechanisms of cells and organs in a more native environment.

Disclosed herein is an example three-dimensional object modeling method. The method may include applying a nonrotating nonuniform electric field to apply a dielectrophoretic torque to a three-dimensional object to rotate the three-dimensional object. Images are captured of the object at different angles during rotation of the object. A three-dimensional model of the object is formed based on the captured images.

Disclosed is an example three-dimensional object modeling system. The system may include a first electrode, a second electrode, a power supply connected to the first electrode and the second electrode, a camera and a controller. The controller may output control signals controlling the power supply such that the first electrode and the second electrode cooperate to apply a nonrotating nonuniform electric field to an object suspended in the fluid so as to rotate the object. The controller may further output control signals controlling the camera to capture images of the object at different angles during rotation of the object, wherein the controller is to form a three-dimensional model of the object based on the captured images.

Disclosed herein is an example cellular object rotation system for use with a cellular object imaging system. The cellular object rotation system may include a first electrode, a second electrode, a power supply connected to the first electrode and the second electrode and a controller to output control signals controlling the power supply such that the first electrode and the second electrode cooperate to apply a nonrotating nonuniform electric field to a cellular object suspended in the fluid so as to rotate the object.

FIG. 1 schematically illustrates portions of an example object rotation system 20 for use with a three-dimensional imaging system. In one implementation, the object rotation system 20 comprises a cellular object rotation system for use with a cellular object imaging system. Object rotation system 20 facilitates low cost and less complex rotation of objects, such as cellular objects, as such object are being imaged for three-dimensional modeling. Object rotation system 20 comprises electrodes 60, power supply 61 and controller 62.

Electrodes 60 comprise a pair of spaced electrodes that cooperate to form a nonrotating nonuniform electric field through a cellular object suspension region 50. The cellular object suspension region 50 comprises a volume of fluid 54 in which a three-dimensional object, such as a cellular object 52 is suspended. In the example illustrated, electrodes 60 comprise a pair of electrodes located on one side of the cellular object 52. In implementations where imaging is performed through the plane or planes containing electrodes 60, such electrodes 60 may be formed from a transparent electrically conductive material such as indium tin oxide. In other implementations, electrodes may be formed from other electrically conductive materials. In one implementation electrodes 62 each comprise a flat planar electrode, wherein the electrodes 60 are coplanar. As a result, object rotation system 20 may be more compact.

Power supply 61 comprise a source of power for allegedly charging at least one of electrodes 60. In one implementation, power supply 61 supplies power to electrodes 60 under the control of controller 62.

Figure 2:
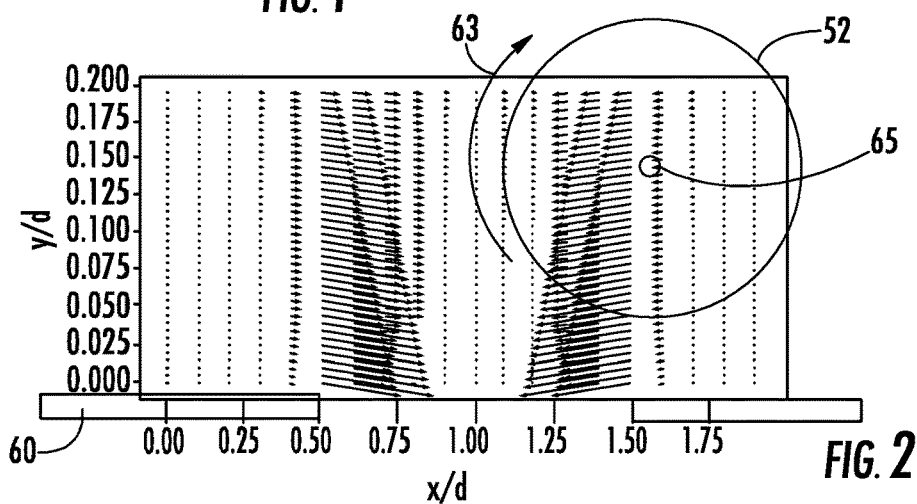
FIG. 2 is a diagram illustrating the example rotation system of FIG. 1 applying a nonrotating nonuniform electric field to rotate an example object.

Controller 62 comprises a processing unit that follows instructions contained in a non-transitory computer-readable medium. In one implementation, controller 62 may comprise an application-specific integrated circuit. In one implementation, controller 62 serves as a signal generator controlling the frequency and voltage of the nonrotating nonuniform electric field. FIG. 2 is a schematic diagram illustrating the application of the nonrotating nonuniform electric field to the example cellular object 52. As indicated by arrow 63, the electric field applies a dielectrophoretic torque to object 52 so as to rotate object 52 about a rotational axis 65. Such rotation facilitates the capturing of images of the cellular object 52 at different angles to facilitate three-dimensional reconstruction or modeling of cellular object 52 for analysis. In one implementation, controller 62 outputs control signals such that electrodes 60 apply a sinusoidal nonrotating nonuniform alternating current electric field having a frequency of at least 30 kHz and no greater than 500 kHz. In one implementation, the nonrotating nonuniform electric field has a voltage of at least 0.1 V rms and no greater than 100 V rms. Between taking consecutive images, the cellular object must have rotated a distance that at least equals to the diffraction limit dlim of the imaging optics. The relationship between minimum rotating angle $\theta min$, radius r and diffraction limit distance dlim is $\theta min = dlim/r$. For example, for imaging with light of $\lambda = 500$ nm and a lens of 0.5 NA, the diffraction limit $dlim = \lambda/(2NA) = 500$ nm. In the meanwhile, the cellular object cannot rotate too much that there is no overlap between consecutive image frames. So the maximum rotating angle between consecutive images $\theta max = 180 - \theta min$.

In one implementation, the nonuniform nonrotating electric field produces a dielectrophoretic torque on the cellular object so as to rotate the cellular object at a speed such that an image may be captured every 2.4 degrees while producing output in a reasonably timely manner. In one implementation where the capture speed of the imager is 30 frames per second, the produced dielectrophoretic torque rotates the cellular object at a rotational speed of at least 12 rpm and no greater than 180 rpm. In one implementation, the produced dielectrophoretic torque rotates the cellular object at least one pixel shift between adjacent frames, but where the picture shift is not so great so as to not be captured by the imager 280. In other implementations, cellular object 52 may be rotated at other rotational speeds.

Figure 3:
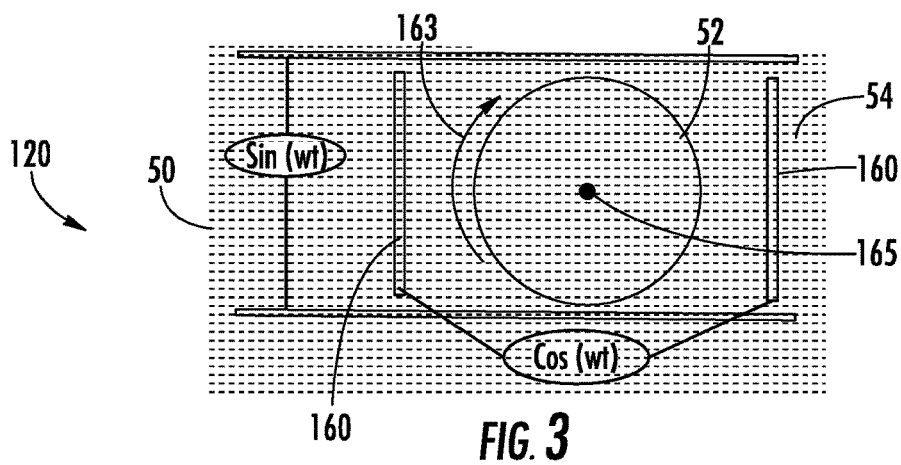
FIG. 3 is a diagram illustrating an example rotation system applying a nonrotating nonuniform electric field to rotate an example object.

FIG. 3 illustrates portions of another example three-dimensional object rotation system 120. As with object rotation system 20, object rotation system 120 is well-suited for rotating very small objects while such small objects are suspended in a fluid. As with object rotation system 20, object rotation system 120 well-suited for rotating cellular objects as such objects are being imaged to form three-dimensional reconstructions or models of the cellular objects. System 120 is similar to system 20 described above except that system 120 comprises an alternative arrangement having electrodes 160 in lieu of electrodes 60. Those remaining components of system 120 which correspond to components of system 20 are numbered similarly in FIG. 3 or are shown in FIG. 1.

Electrodes 160 comprise a pair of electrodes that cooperate to form a nonrotating nonuniform electric field through the cellular object suspension region 50. In the example illustrated, electrodes 160 comprise a pair of electrodes located on opposite sides of the cellular object 52 with the electrodes 160 facing one another. In implementations where imaging of the rotating cellular object is with an imager or having an optical axis that passes through or intersects either of the two electrodes, such electrodes may be formed from a transparent or translucent electrically conductive material such as indium tin oxide. In other implementations, electrodes 160 may form from other electrically conductive materials.

In operation, object rotation system 120 may perform in a similar fashion as compared object rotation system 20. Controller 62 (shown in FIG. 1) outputs control signals or generate signals such that electrodes 160 apply a nonrotating nonuniform electric field about the suspended object, shown as cellular object 52. In one implementation, controller 162 outputs control signals such that electrodes 160 apply a sinusoidal nonrotating nonuniform alternating current electric field having a frequency of at least 30 kHz and no greater than 500 kHz. In one implementation, the nonrotating nonuniform electric field has a voltage of at least 0.1 V rms and no greater than 100 V rms.

The electric field is applied such that it applies a dielectrophoretic torque to the object 52 so as to rotate the object 52 as indicated by arrow 163 about an axis 165. The rotational axes 165 of object 52 is parallel to the slide, stage or platform containing the fluid and may be perpendicular to the optical axis of the image or camera capturing images of object 52 at different angular positions. Because the rotation axis is perpendicular to the optical axis, the overall imaging system may be more compact and less complex.

Figure 4:
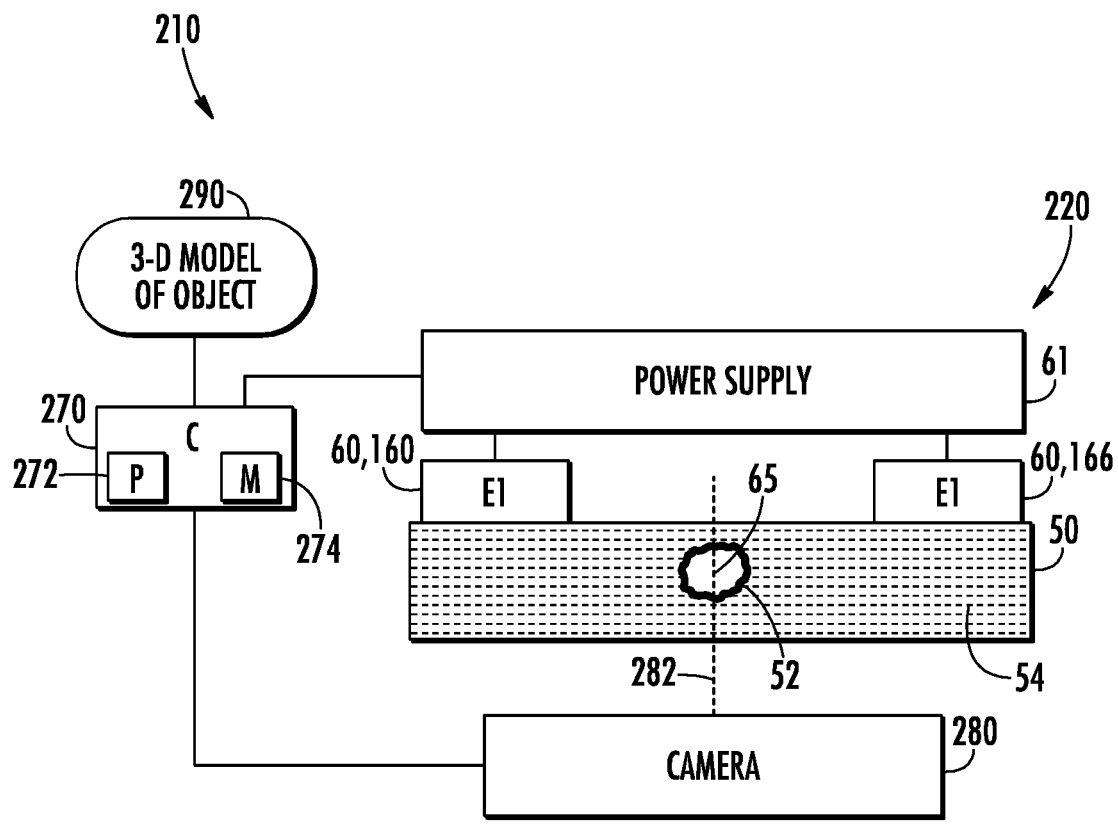
FIG. 4 is a schematic diagram illustrating portions of an example three-dimensional object modeling system.

FIG. 4 schematically illustrates portions of an example three-dimensional object modeling system 210. Modeling system 210 facilitates the rotation of an object, such as a cellular object, as the object is being imaged to facilitate the output of a three-dimensional reconstruction or model of the object. Modeling system 210 facilitates such rotation of the object with an architecture that is less complex and more compact, potentially reducing cost. Modeling system 210 comprises object rotation system 220, controller 270 and imager 280, in the form of a camera.

Object rotation system 220 is similar to object rotation system 20 described above except that controller 270 controls power supply 61 and imager 280. Controller 270 comprises processing unit 272 and a non-transitory computer readable medium in the form of memory 274. Processing unit 272 follows instructions contained in memory 274. Memory 274 contains instructions that direct processing unit 272 to control the operation of electrodes 60, 160 and imager 280. For example, controller 270 outputs control signals controlling the rate at which so the object 52 is rotated during imaging. As with controller 62, controller 270 serves as a signal generator controlling the frequency and voltage of the nonrotating nonuniform electric field such as shown in FIG. 2 or 3. The electric field applies a dielectrophoretic torque to object 52 so as to rotate object 52 about a rotational axis 65. Such rotation facilitates the capturing of images of the cellular object 52 at different angles to facilitate three-dimensional reconstruction or modeling of cellular object 52 for analysis. In one implementation, controller 270 outputs control signals such that electrodes 60, 160 apply a sinusoidal nonrotating nonuniform alternating current electric field having a frequency of at least 30 kHz and no greater than 500 kHz. In one implementation, the nonrotating nonuniform electric field has a voltage of at least 0.1 V rms and no greater than 100 V rms. Between taking consecutive images, the cellular object must have rotated a distance that at least equals to the diffraction limit $d_{lim}$ of the imaging optics. The relationship between minimum rotating angle $\theta_{min}$, radius r and diffraction limit distance $d_{lim}$ is $\theta_{min}=d_{lim}/r$. For example, for imaging with light of $\lambda=500$ nm and a lens of 0.5 NA, the diffraction limit $d_{lim}=\lambda/(2NA)=500$ nm. In the meanwhile, the cellular object cannot rotate too much that there is no overlap between consecutive image frames. So the maximum rotating angle between consecutive images $\theta_{max}=180-\theta_{min}$.

In one implementation, the nonuniform nonrotating electric field produces a dielectrophoretic torque on the cellular object so as to rotate the cellular object at a speed such that an image may be captured every 2.4 degrees while producing output in a reasonably timely manner. In one implementation where the capture speed of the imager is 30 frames per second, the produced dielectrophoretic torque rotates the cellular object at a rotational speed of at least 12 rpm and no greater than 180 rpm. In one implementation, the produced dielectrophoretic torque rotates the cellular object at least one pixel shift between adjacent frames, but where the picture shift is not so great so as to not be captured by the imager 280. In other implementations, cellular object 52 may be rotated at other rotational speeds.

Imager 280 comprise at least one camera to capture images of the rotating cellular object 52 at different angles during rotation of cellular object 52 about axis 65. Imager 280 has an optical axis 282 which is perpendicular to axis 65. In one implementation, imager 280 may comprise multiple cameras. Imager 280 captures images of the rotating cellular object 52 at different angular positions during his rotation to facilitate subsequent three-dimensional image reconstruction of the cellular object 52 as will be described hereafter. In one implementation imager 280 may comprise a camera having an optical lens 282 facility microscopic viewing and imaging of cellular object 52.

In addition to outputting control signals to electrodes 60, 160 so as to create the nonrotating nonuniform electric field that rotates cellular object 52, controller 270 may additionally control imager 280. Controller 270 receives images or image signals from imager 280. Based upon the different images of the rotating cellular object 52 captured at different rotational angles, controller 270 triangulates identified points of the image to form a three-dimensional reconstruction or model 290 of cellular object 52 for analysis.

Figure 5:
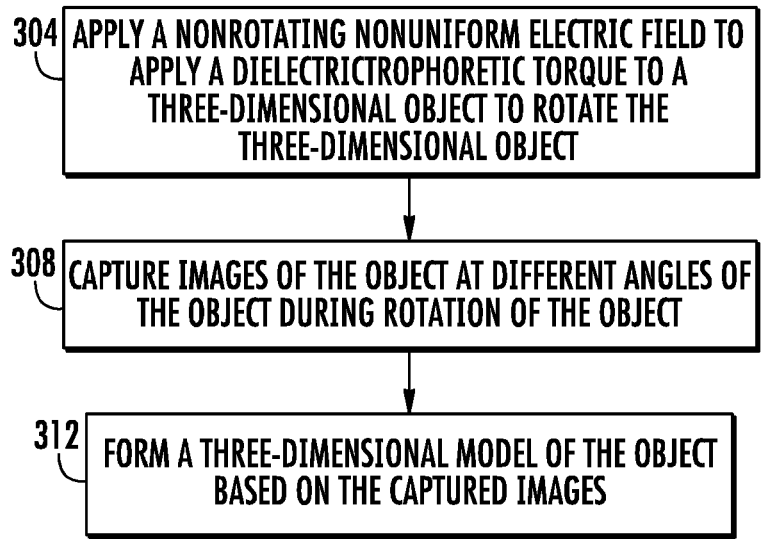
FIG. 5 is a flow diagram of an example three-dimensional object modeling method.

FIG. 5 is a flow diagram of an example three-dimensional object modeling method 300. Modeling method 300 captures images of an object rotated with a nonrotating nonuniform electric field. Modeling method 300 may be implemented with less complex and lower-cost components. Although method 300 is described in the context of being carried out by three-dimensional object modeling system 210 having object rotation system 220, it should be appreciated that method 300 may likewise be carried out with other similar modeling systems and other similar object rotation systems, such as object rotation systems 20 or 120.

As indicated by block 304, a nonrotating nonuniform electric field is applied so as to apply a dielectrophoretic torque to a three-dimensional object, such as a cellular object, to rotate the three-dimensional object. In one implementation, a sinusoidal nonrotating nonuniform alternating current electric field having a frequency of at least 30 kHz and no greater than 500 kHz is applied to the object or the object suspended in a fluid. In one implementation, the nonrotating nonuniform electric field has a voltage of at least 0.1 V rms and no greater than 100 V rms.

As indicated by block 308, controller 270 outputs control signals causing camera 282 capture images of the object 52 at different angles during rotation of object 52. As indicated by block 312, upon receiving the captured images from imager 280, controller 270 formed a three-dimensional reconstruction or model of the object 52 based upon the captured images.

Figure 6:
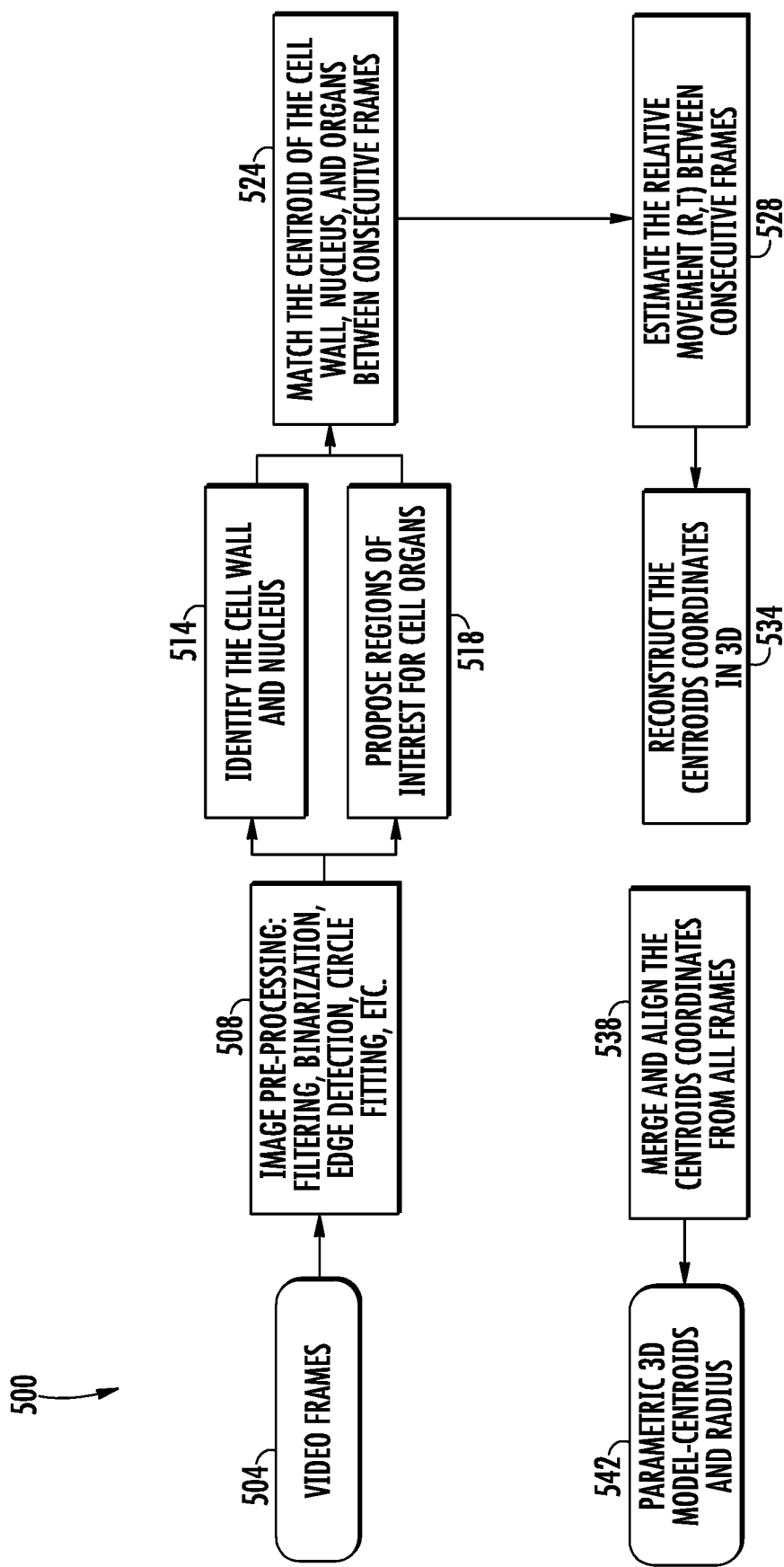
FIG. 6 a flow diagram of an example three-dimensional volume modeling method.

FIG. 6 is a flow diagram of an example three-dimensional volumetric modeling method 500 that may be carried out by controller 470 using captured two-dimensional images of the rotating object 52. As indicated by block 504, a controller, such as controller 470, receives video frames or two-dimensional images captured by the imager/camera 60 during rotation of object 52. As indicated by block 508, various preprocessing actions are taken with respect to each of the received two-dimensional image video frames. Such preprocessing may include filtering, binarization, edge detection, circle fitting and the like.

As indicated by block 514, utilizing such edge detection, circle fitting and the like, controller 470 retrieves and consults a predefined three-dimensional volumetric template of the object 52, to identify various internal structures of the object are various internal points in the object. The three-dimensional volumetric template may identify the shape, size and general expected position of internal structures which may then be matched to those of the two-dimensional images taken at the different angles. For example, a single cell may have a three-dimensional volumetric template comprising a sphere having a centroid and a radius. The three-dimensional location of the centroid and radius are determined by analyzing multiple two-dimensional images taken at different angles.

Based upon a centroid and radius of the biological object or cell, controller 470 may model in three-dimensional space the size and internal depth/location of internal structures, such as the nucleus and organelles. For example, with respect to cells, controller 470 may utilize a predefined template of a cell to identify the cell wall and the nucleus As indicated by block 518, using a predefined template, controller 470 additionally identifies regions or points of interest, such as organs or organelles of the cell. As indicated by block 524, controller 470 matches the centroid of the cell membrane, nucleus and organelles amongst or between the consecutive frames so as to estimate the relative movement (R, T) between the consecutive frames per block 528.

As indicated by block 534, based upon the estimated relative movement between consecutive frames, controller 470 reconstructs the centroid coordinates in three-dimensional space. As indicated by block 538, the centroid three-dimensional coordinates reconstructed from every two frames are merged and aligned. A single copy of the same organelle is preserved. As indicated by block 542, controller 470 outputs a three-dimensional volumetric parametric model of object 52.

FIGS. 7-11 illustrate one example modeling process 600 that may be utilized by 3-D modeler 70 or controller 470 in the three-dimensional volumetric modeling of the biological object. FIG. 7-11 illustrate an example three-dimensional volumetric modeling of an individual cell. As should be appreciated, the modeling process depicted in FIGS. 7-11 may likewise be carried out with other biological objects.

As shown by FIG. 6, two-dimensional video/camera images or frames 604A, 604B and 604C (collectively referred to as frame 604) of the biological object 52 (schematically illustrated) are captured at different angles during rotation of object 52. In one implementation, the frame rate of the imager or camera is chosen such as the object is to rotate no more than 5° per frame by no less than 0.1°. In one implementation, a single camera captures each of the three frames during rotation of object 52 (schematically illustrated with three instances of the same camera at different angular positions about object 52) in other implementations, multiple cameras may be utilized.

As shown by FIGS. 7 and 8, after image preprocessing set forth in block 508 in FIG. 5, edge detection, circle fitting another feature detection techniques are utilized to distinguish between distinct structures on the surface and within object 52, wherein the structures are further identified through the use of a predefined template for the object 52. For the example cell identify the cell, controller 470 identifies wall 608, its nucleus 610 and internal points of interest, such as cell organs or organelles 612 in each of the frames (two of which are shown by FIGS. 7 and 8).

As shown by FIG. 9 and as described above with respect to blocks 524-538, controller 470 matches a centroid of a cell membrane, nucleus and organelles between consecutive frames, such as between frame 604A and 604B. Controller 470 further estimates a relative movement between the consecutive frames, reconstructs a centroid's coordinates in three-dimensional space and then utilizes the reconstructed centroid coordinates to merge and align the centroid coordinates from all of the frames. The relationship for the relative movement parameters R and T is derived, assuming that the rotation axis is kept still, and the speed is constant all the time. Then, just the rotation speed is utilized to determine R and T $(\overrightarrow{O_1O_2})$ as shown in FIG. 9, where:

$$\overrightarrow{O_1O_2} = \overrightarrow{OO_1} \cdot R_\theta - \overrightarrow{OO_1}$$

$$R_\theta = R_y(\theta) = \begin{bmatrix} \cos\theta & 0 & \sin\theta \\ 0 & 1 & 1 \\ -\sin\theta & 1 & \cos\theta \end{bmatrix}$$

based on the following assumptions:
θ is constant;
$|\overrightarrow{OO_1}|=|\overrightarrow{OO_2}|=|\overrightarrow{OO_3}|=\ldots$ ;
rotation axis doesn't change (along y axis); and
$\overrightarrow{OO_1}$ is known.

As shown by FIG. 10, the above reconstruction by controller 470 results in the output of a parametric three-dimensional volumetric model of the object 52, shown as a cell.

Although the present disclosure has been described with reference to example implementations, workers skilled in the art will recognize that changes may be made in form and detail without departing from the spirit and scope of the claimed subject matter. For example, although different example implementations may have been described as including features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A three-dimensional object modeling method comprising:
    applying a nonrotating nonuniform electric field to apply a dielectrophoretic torque to a three-dimensional object to rotate the three-dimensional object;
    capturing images of the object at different angles of the object during rotation of the object; and
    forming a three-dimensional model of the object based on the captured images, wherein forming the three-dimensional model of the object based on the captured images further comprises matching the captured images to a three-dimensional volumetric template corresponding to the rotating object.

\* \* \* \* \*